United States Patent
McVey et al.

(10) Patent No.: US 7,157,046 B2
(45) Date of Patent: *Jan. 2, 2007

(54) HIGH CAPACITY FLASH VAPOR GENERATION SYSTEMS

(75) Inventors: Iain F. McVey, Lakewood, OH (US);
Francis J. Zelina, Lake City, PA (US);
Aaron L. Hill, Erie, PA (US); Gerald E. McDonnell, Basingstoke (GB);
Kevin O. Williams, Solon, OH (US);
Thaddeus Mielnik, Concord, OH (US)

(73) Assignee: Steris Inc., Temecula, CA (US)

( * ) Notice: Subject to any disclaimer, the term of this patent is extended or adjusted under 35 U.S.C. 154(b) by 760 days.

This patent is subject to a terminal disclaimer.

(21) Appl. No.: 10/047,317

(22) Filed: Jan. 14, 2002

(65) Prior Publication Data

US 2002/0114727 A1 Aug. 22, 2002

Related U.S. Application Data

(60) Provisional application No. 60/269,659, filed on Feb. 16, 2001.

(51) Int. Cl.
*A61L 2/00* (2006.01)
(52) U.S. Cl. ............... 422/28; 422/3; 422/298; 422/306
(58) Field of Classification Search ............ 422/3, 422/28, 62, 123, 125, 305, 306, 307, 298, 422/26; 126/365.1
See application file for complete search history.

(56) References Cited

U.S. PATENT DOCUMENTS

| | | | | |
|---|---|---|---|---|
| 3,531,908 A | * | 10/1970 | Rausing et al. | 53/426 |
| 5,445,792 A | * | 8/1995 | Rickloff et al. | 422/28 |
| 5,872,359 A | | 2/1999 | Stewart et al. | 250/339.12 |
| 5,876,664 A | | 3/1999 | Childers et al. | 422/28 |
| 5,949,958 A | | 9/1999 | Naperkowski et al. | 392/399 |
| 6,077,480 A | | 6/2000 | Edwards et al. | 422/28 |
| 6,645,429 B1 | * | 11/2003 | Raniwala | 422/28 |
| 6,702,985 B1 | * | 3/2004 | Taggart et al. | 422/28 |
| 2002/0122838 A1 | * | 9/2002 | Anderson et al. | 425/149 |

FOREIGN PATENT DOCUMENTS

EP  336 047  10/1989

* cited by examiner

*Primary Examiner*—Krisanne Jastrzab
(74) *Attorney, Agent, or Firm*—Fay, Sharpe, Fagan, Minnich & McKee, LLP

(57) ABSTRACT

A flash vaporizer (34) provides a constant flow of vaporized hydrogen peroxide or other antimicrobial compounds for rapidly sterilizing large enclosures (10), such as rooms or buildings. The vaporizer includes a heated block (50) which defines an interior bore or bores (70, 72, 74). The flowpath created by the bore or bores increases in cross sectional area as the hydrogen peroxide passes through the block to accommodate the increase in volume during the conversion from liquid to gas. The vapor is injected into dry air in a duct that circulates it to the large enclosure.

33 Claims, 7 Drawing Sheets

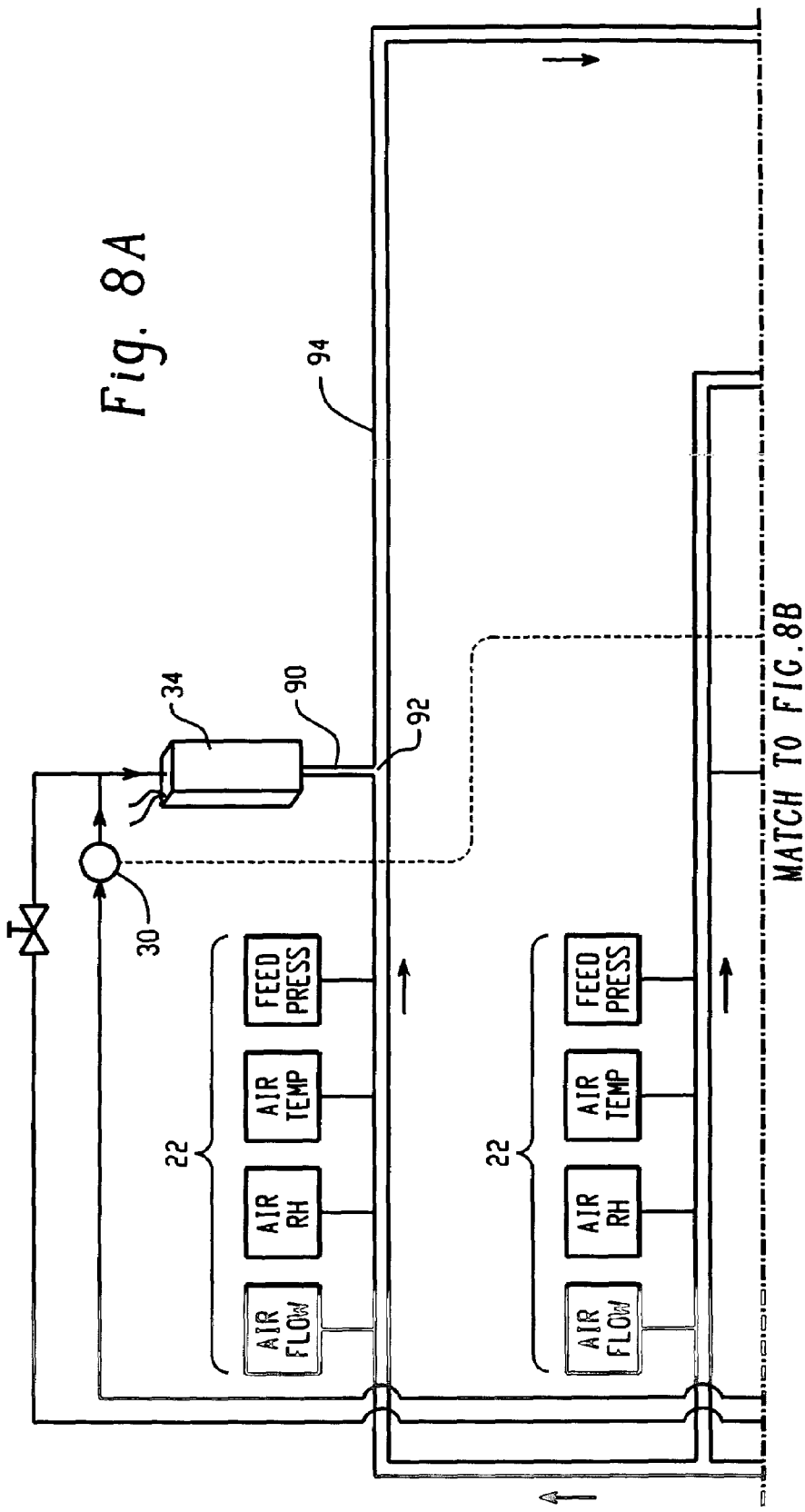

HIGH CAPACITY FLASH VAPOR GENERATION SYSTEMS

This application claims the benefit of U.S. provisional patent application Ser. No. 60/269,659, filed Feb. 16, 2001.

BACKGROUND OF THE INVENTION

The present invention relates to the sterilization arts. It finds particular application in conjunction with hydrogen peroxide vapor systems used in connection with the sterilization of rooms, buildings, large enclosures, and bottling, packaging, and other production lines and will be described with particular reference thereto. It should be appreciated, however, that the invention is also applicable to other chemical vaporization systems such as those employing other peroxy compounds or aldehydes, for example, peracetic acid or formaldehyde vaporization systems.

Microbial decontamination of rooms and buildings can be achieved using chlorine dioxide gas. However, chlorine dioxide is highly toxic and must be recovered from the microbial decontamination process. Recovery of toxic gases from dilution air, leaking air, and the degassing of gas absorptive materials in the decontaminated room or building is difficult and time consuming. Further, care must be taken and monitors placed to insure that the toxic gas does not escape into the surrounding areas.

Sterile enclosures and other clean rooms are used by hospitals and laboratories for conducting tests in a microorganism-free environment. Further, a variety of medical, pharmaceutical, dental, and food packaging items are sterilized prior to use or reuse, in various forms of enclosures. Processing equipment for pharmaceuticals and food, freeze driers, meat processing equipment typically housed or moveable into large enclosures, or even rooms are advantageously sterilized.

Vaporized hydrogen peroxide is a particularly useful sterilant for these purposes because it is effective at low temperatures. Keeping the temperature of the enclosure near room temperature eliminates the potential for thermal degradation of associated equipment and items to be sterilized within the enclosure. In addition, hydrogen peroxide readily decomposes to water and oxygen, which, of course, are not harmful to the humans including technicians, people nearby, or people subsequently entering the treated space.

For optimally effective sterilization, the hydrogen peroxide is maintained in the vapor state. Sterilization efficiency is reduced by condensation. Several different methods have been developed for delivering a vapor phase sterilant to an enclosure or chamber for sterilizing the load (e.g., medical instruments) or interior thereof. In one option, the "deep vacuum" approach, a deep vacuum is used to pull liquid sterilant into a heated vaporizer. Once vaporized, the sterilant diffuses by its vapor pressure into an evacuated and sealed chamber. In another option, the "flow-through" approach, vaporized sterilant is vaporized in a flow of carrier gas, such as air, that serves to deliver the sterilant into, through, and out of the chamber, which may be at a slightly negative or positive pressure. A solution of about 35% hydrogen peroxide in water is injected into the vaporizer as fine droplets or mist through injection nozzles. The droplets fall on a flat heated surface which heats the droplets to form the vapor, without breaking it down to water and oxygen. A carrier gas is circulated over the heat transfer surface to absorb the peroxide vapor.

As the size of the enclosure increases, or the demand for hydrogen peroxide is increased, the efficiency of the vaporization system becomes more significant. The capacity of the vaporizer is limited in a number of ways. First, the vaporization process creates a pressure increase, reducing the flow of air through the vaporizer. This increases the sterilization time and effectively limits the size of the enclosure to one which is capable of sterilization within an acceptable time period. Second, to maintain sterilization efficiency, the pressure at which the vapor is generated is limited to that at which the hydrogen peroxide is stable in the vapor state.

One solution has been to increase the size of the vaporizer, the injection rate of hydrogen peroxide into the vaporizer, and the flow rate of carrier gas. However, the carrier gas tends to cool the heating surface, disrupting the vaporization process. Heating the heating surface to a higher temperature breaks down the peroxide.

Yet another solution is to use multiple vaporizers to feed a single enclosure. The vaporizers may each be controlled independently, to allow for variations in chamber characteristics. However, the use of multiple vaporizers adds to the cost of the system and requires careful monitoring to ensure that each vaporizer is performing with balanced efficiency.

The present invention provides a new and improved vaporization system and method which overcomes the above-referenced problems and others.

SUMMARY OF THE INVENTION

In accordance with one aspect of the present invention, a hydrogen peroxide vaporization system is provided. The system includes a block having an internal bore or bores which create a fluid flowpath through the block. A solution of hydrogen peroxide in water is passed along the flowpath. Increases in volume of the sterilant as it changes from liquid to vapor are accommodated by a progressively increasing size of the flowpath.

In accordance with another aspect of the present invention, a method of hydrogen peroxide vaporization is provided.

In accordance with another aspect of the present invention, a method of decontaminating an enclosure is provided. The method includes providing a first carrier gas stream and a second carrier gas stream, the first stream having a lower flow rate than the second stream. The first stream is introduced to a passage having at least one bend. A flow of an aqueous solution of a peroxy compound is introduced into the passage upstream of the bend. The peroxy compound mixes with the first stream. Walls of the passage are heated to vaporize the aqueous solution. The vaporized aqueous solution and first carrier gas stream is mixed with the second carrier gas stream in a mixing zone downstream of the passage and transported to the enclosure.

One advantage of the present invention is that a high output of vaporized hydrogen peroxide is achieved.

Another advantage of the present invention is that the air flow and hydrogen peroxide injection rates can be increased.

Another advantage resides in the ability to decontaminate larger volumes.

Another advantage of the present invention is that it enables peroxide concentration levels to be raised rapidly to sterilization levels, particularly when used with smaller enclosures, thereby reducing the conditioning time.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
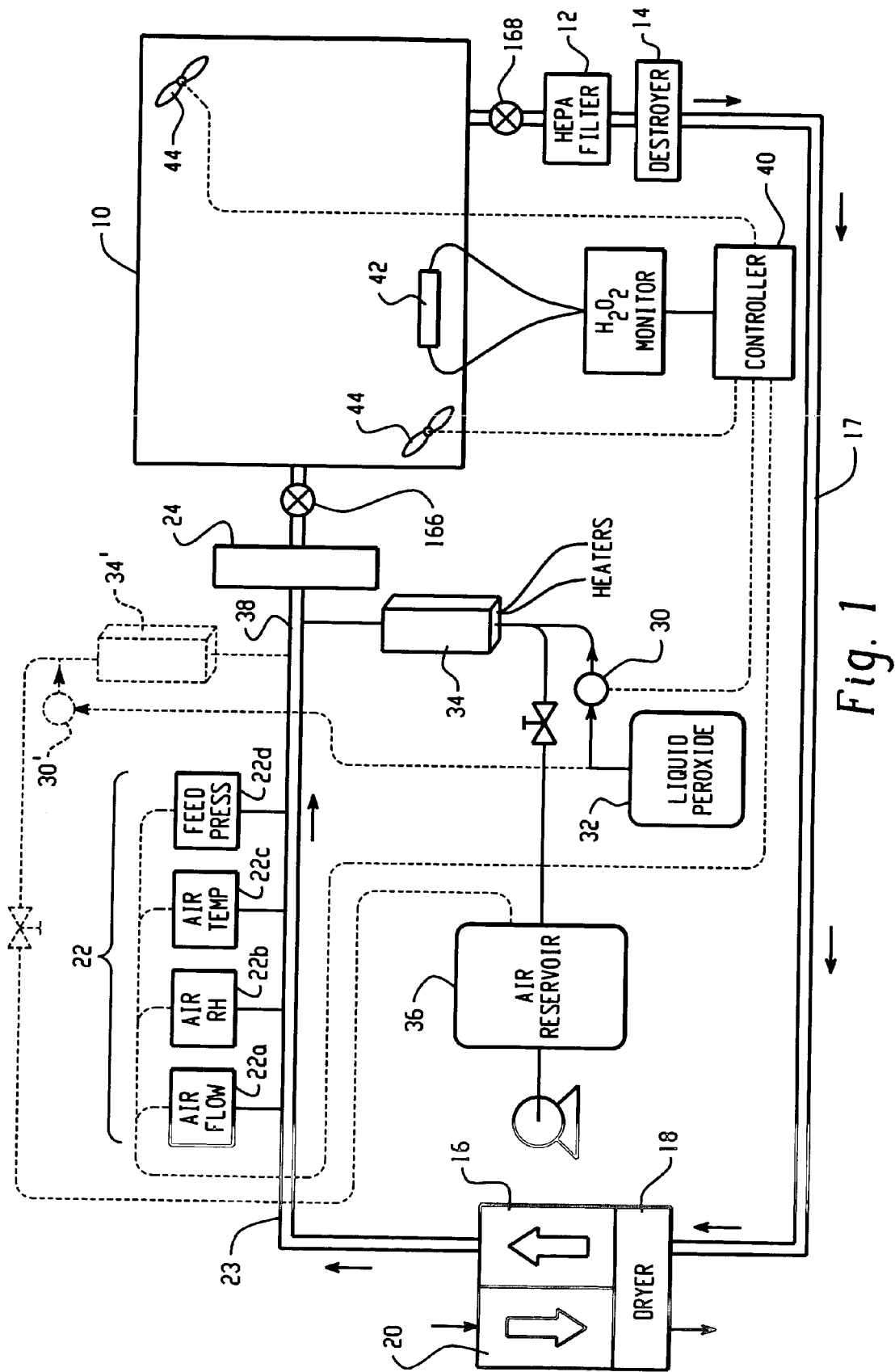
FIG. 1 is a schematic view of a preferred embodiment of a hydrogen peroxide vaporization system in accordance with the present invention.

With reference to FIG. 1, a system for microbially decontaminating a room or other defined area with an antimicrobial vapor is shown. While the system is described with particular reference to hydrogen peroxide in vapor form, other antimicrobial vapors are also contemplated, such as vapors comprising peracetic acid or other peroxy compounds, aldehydes, such as formaldehyde vapors, and the like. Air from a large defined region, such as a room 10 with a volume on the order of 1,000–4,000 cubic meters is withdrawn through a contamination removing filter 12 and a peroxide destroying catalyst 14 by a blower 16, which is connected with the filter and destroyer by a duct or line 17. The blower draws the air through a dryer, such as a desiccant wheel 18 which removes the water vapor. A second blower 20 blows heated air through a saturated portion of the desiccant wheel to remove and exhaust the absorbed moisture to the atmosphere. This heating process preferably heats the recirculated air from the ambient temperature of the room, typically about 20°–40° C. A series of air quality meters 22 monitor the dried air leaving the blower to determine its hydrogen peroxide vapor absorption capacity. The air is returned to the room 10 through a duct or line 23 and another microbe blocking filter 24, such as a HEPA filter. Optionally, the duct work includes all or a portion of a pre-existing HVAC system. Upon initially starting a decontamination process, the air is circulated through the dryer for a sufficient duration to bring the relative humidity in the room down to an acceptable level, preferably below 20% relative humidity. For sealed enclosures, pressure control within the enclosure may be appropriate. For rooms, pressure control is not essential and would be addressed on a case-by-case basis. In clean rooms and the like, where drawing potentially contaminated air into the room is to be avoided, the pressure in the room is maintained above ambient.

Once the room has been brought to a sufficiently low relative humidity, an antimicrobial vapor is injected into the air. The antimicrobial vapor includes hydrogen peroxide vapor in the preferred embodiment, although other antimicrobial vapors or mixtures of antimicrobial vapors are also contemplated. More specifically, a means for introducing liquid hydrogen peroxide, such as an injection pump 30, pressurized container, gravity feed system, or the like, deposits hydrogen peroxide, preferably in the form of a liquid flow or spray, from a reservoir 32, such as a large drum, into a flash vaporizer 34. The liquid hydrogen peroxide includes a mixture of hydrogen peroxide in a diluent, such as water, preferably an aqueous mixture comprising about 30–40% by weight hydrogen peroxide in water. Optionally, a carrier gas, such as air, nitrogen, carbon dioxide, helium, argon, or a combination of carrier gases, is fed into the flash vaporizer concurrently with the hydrogen peroxide liquid to assist in propelling the peroxide vapor through the flash vaporizer and injecting it into the carrier gas flow. In a preferred embodiment, the carrier gas includes pressurized air from an air reservoir 36. The exact pressure varies with the production rate, the length and restrictiveness of passages in the flash vaporizer, and the like, and typically varies from 1.0–2.0 atmospheres absolute ($1.013 \times 10^5$– $2.026 \times 10^5$ Pascals absolute), i.e, about 0–1 atm. gauge ($0$–$1.013 \times 10^5$ Pascals gauge), more preferably, about $6$–$14 \times 10^3$ Pa. An advantage of using such a carrier gas centers on the fact that the liquid hydrogen peroxide is unlikely to continuously impinge on the same point in the vaporizer. The more dispersed the liquid hydrogen peroxide is within the vaporizer, the more readily the peroxide will be vaporized. In addition, with a well dispersed hydrogen peroxide injection, the less likely that specific regions of the vaporizer will experience undue cooling thereby hindering the vaporization process.

The carrier gas tends to cool the vaporizer, reducing the rate at which the aqueous hydrogen peroxide solution is vaporized. Consequently, it is desirable to maintain the carrier gas at or slightly above a minimum flow rate needed to carry the vaporized hydrogen peroxide through the flash vaporizer 34 without significant degradation of the peroxide vapor, but at a flow rate which is low enough such that appreciable cooling of the vaporizer by the carrier gas does not occur. Accordingly, the flow rate of carrier gas through flash vaporizer 34 is preferably lower than the flow rate of carrier gas which does not pass through flash vaporizer 34. The majority of the carrier gas thus travels from the blower 16 through the duct 23 to a mixing zone 38 downstream of the vaporizer, where both the carrier gas stream and the vapor are combined prior to entering the enclosure. For example, the combined carrier gas streams may have a flow rate of about 20,000 liters/minute, while the carrier gas stream flowing through the flash vaporizer is 100 liters/min or less, more preferably, about 20 liters/min or less, most preferably, about 1–10 liters/min.

A controller 40 is connected with one or more peroxide concentration sensors 42 in the room. The controller controls fans 44 or other devices in the room 10 for adjusting the distribution of hydrogen peroxide vapor for better uniformity.

Based on the measured concentration in the room, the controller 40 controls the injection pump 30 and a feed rate of the air from the air reservoir 36 into flash vaporizer 34. The controller is further connected with air monitors 22 to maintain the injection rate below the saturation point of the circulated air. Preferably, the air quality monitors include an air flow monitor 22a for monitoring a rate of air flow, typically in the range of 20–40 cubic meters per minute. The monitors further include a relative humidity monitor 22b, an air temperature monitor 22c, and a pressure monitor 22d. When the air recirculation ducts are larger in diameter and have a higher air moving capacity, a second flash vaporizer 34' and a second injection pump 30' are connected with the liquid peroxide source 32 and with the air source 36. For larger enclosures, one or more additional air circulation lines with flash vaporizers are provided.

While described with particular reference to hydrogen peroxide, it will be appreciated that the system is also applicable to vaporization of other solutions and pure liquids, such as peracetic acid, other peroxy compounds, and the like.

The term "microbial decontamination" and similar terms, as used herein, encompass sterilization, disinfection, and lesser forms of antimicrobial treatment, such as sanitization. The term is also used to encompass the degradation or deactivation of other harmful biological species, particularly those capable of undergoing conformational changes, such as prions.

Figure 2:
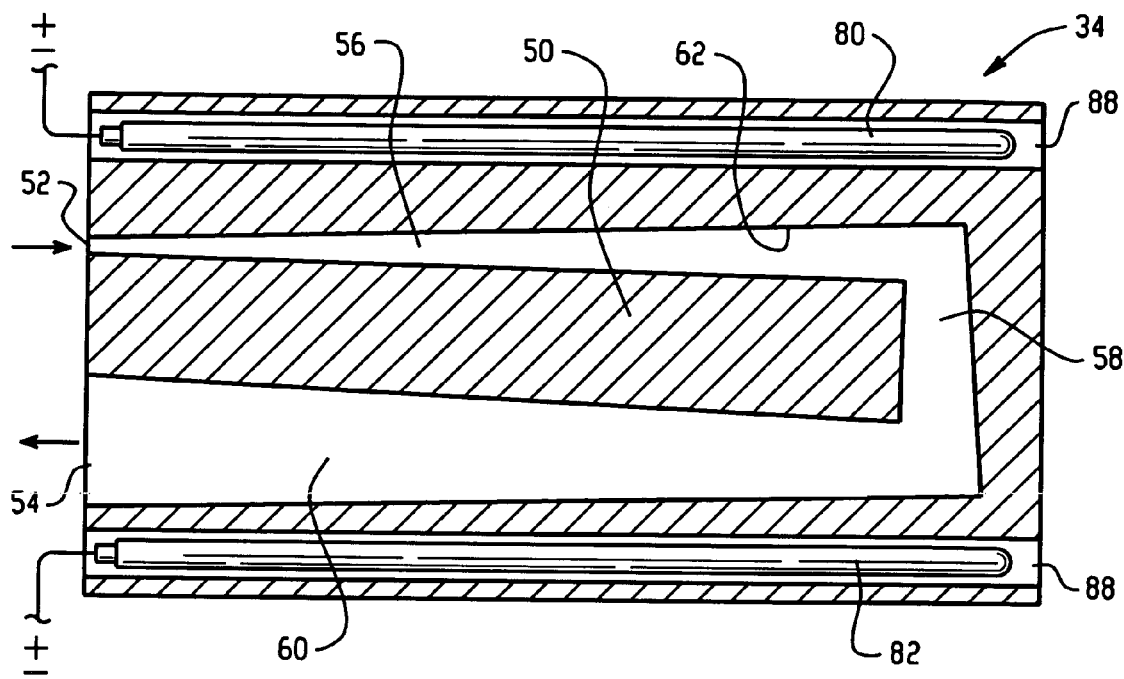
FIG. 2 is a side sectional view of one embodiment of a vaporizer.

With reference also to FIG. 2, the flash vaporizer 34 includes a heated block 50, which is preferably formed from anodized aluminum, or other thermally conductive material resistant to hydrogen peroxide and with which the hydrogen peroxide is compatible, i.e., that does not degrade the hydrogen peroxide. A fluid pathway is defined by a one or series of bores, formed in the block extending from an inlet 52, connected with the supply line, to an outlet 54. In one embodiment, the series of bores 56, 58, 60 progressively increases in internal diameter from the inlet 52 to the outlet 54, thus creating an increasing area of contact and internal volume per unit length. The liquid hydrogen peroxide contacts the walls 62 of the bores and is vaporized. The increasing volume of the vapor/liquid mixture passing through the bore is accommodated by the increasing diameter of the bores.

Figure 3:
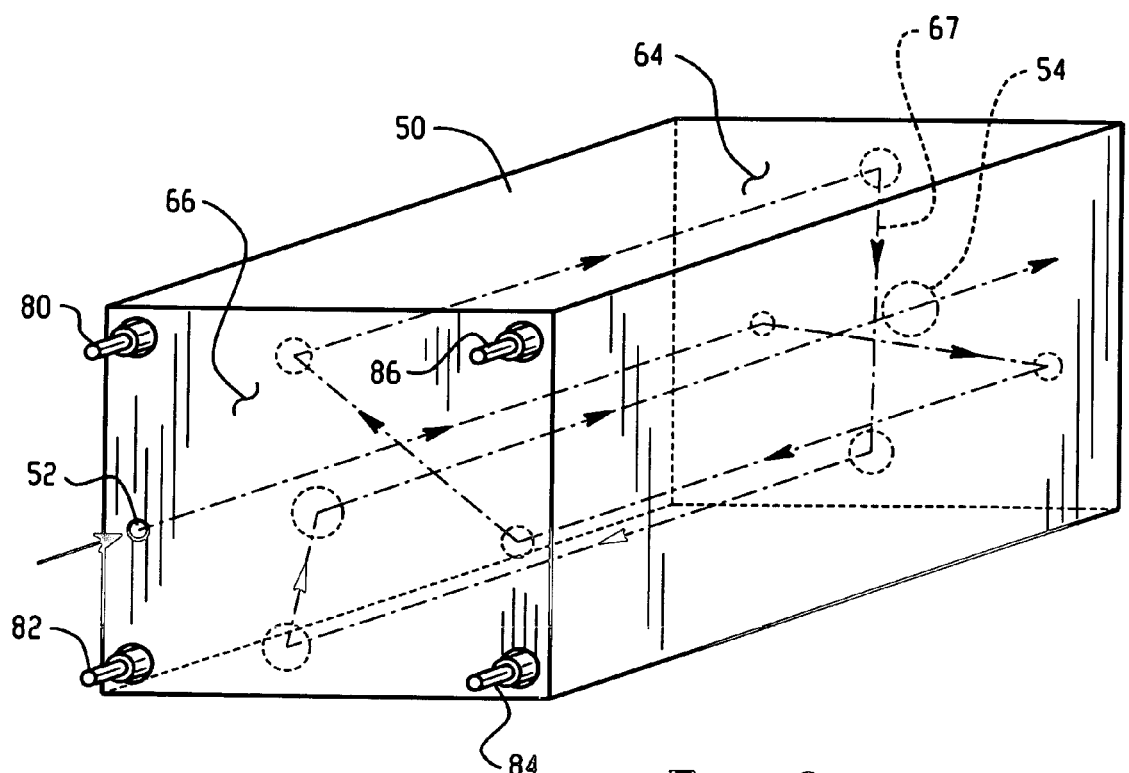
FIG. 3 is a perspective view of the vaporizer of FIG. 2.

In each of the embodiments, the bore may make several turns within the block. For example, starting at the bore inlet 52, the bore makes a U-turn adjacent an outlet end 64 of the block, returns to an inlet end 66 of the block, and makes two more such turns before reaching the outlet 54. Preferably, the turns are formed by sharp, "L-shaped" rather than rounded turns. For example, as shown in FIG. 3, each turn includes two approximately 90° corners and an end wall 67, which turn the bore through approximately 180°. Having generally sharp, rather than rounded corners encourages the flowing liquid/vapor mixture to hit the walls, thereby improving the rate of vaporization.

Figure 4:
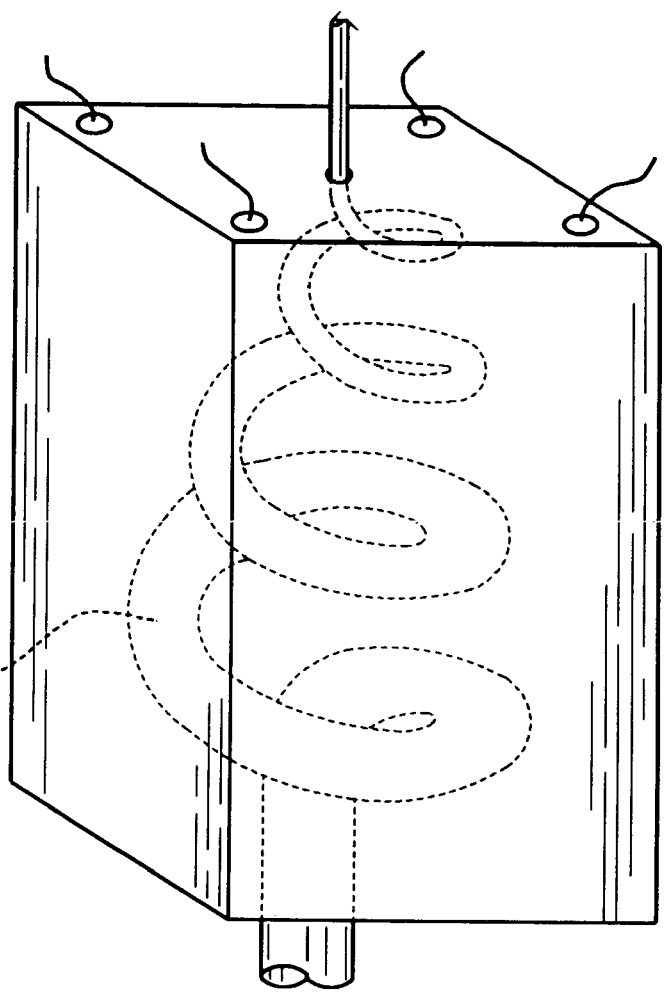
FIG. 4 is a perspective view of a second vaporizer embodiment.

Other arrangements are contemplated, such as a spiral bore 68, as shown in FIG. 4. At each turn, inertia tends to propel fine, suspended droplets into the walls resulting in the vaporization of the droplets. In this manner, any fine droplets of mist or fog are turned to vapor. Preferably, at least two substantially 180° turns are provided in the flowpath to assure this increased contact.

Figure 5:
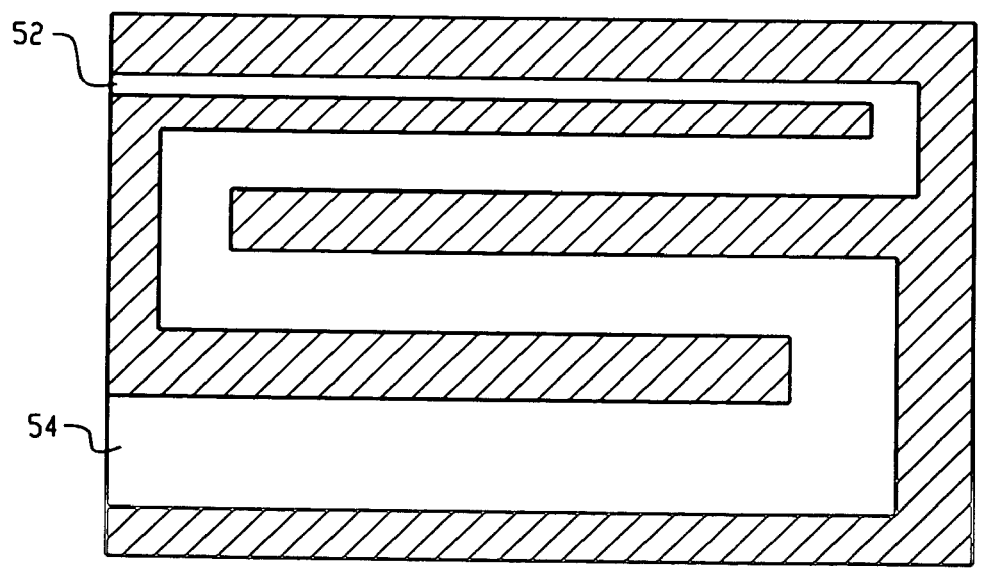
FIG. 5 is a side sectional view of a third vaporizer embodiment.

The increasing diameter may be provided by progressively increasing the diameter of each segment of the bore, as shown in FIG. 2. Alternatively, longitudinal portions of the bore can each be of a single, successively larger diameter, as shown in FIG. 5. Other arrangements for progressively increasing the bore diameter are also contemplated. For example, baffles or fins may be provided adjacent the inlet to reduce the available flow space while increasing heated surface area.

Figure 6:
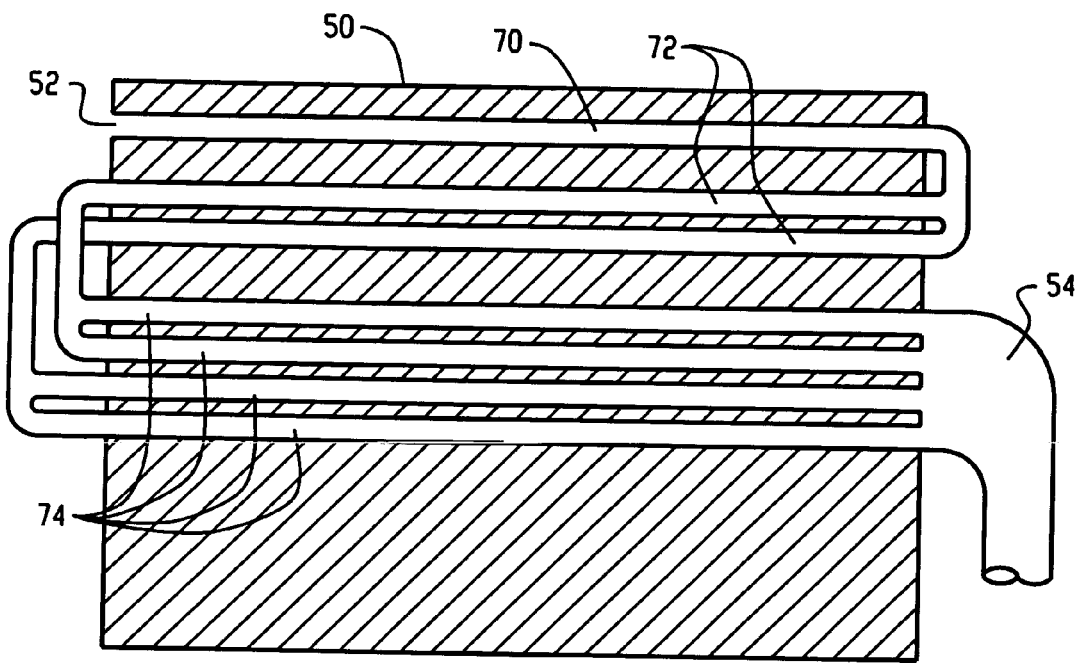
FIG. 6 is a side sectional view of a fourth vaporizer embodiment.

In the embodiment of FIG. 6, the number of bore portions increases with each pass through the block. For example, a single longitudinal bore 70 defines the first pass, two or more bore portions 72 define the second pass. Each of the second bores is preferably connected with more bores 74 for a third pass, and so forth. In this way, as for the earlier embodiments, the cross sectional area of the fluid pathway created by the bores increases as the hydrogen peroxide travels from the inlet to the outlet (in this case, a plurality of outlets).

Figure 7:
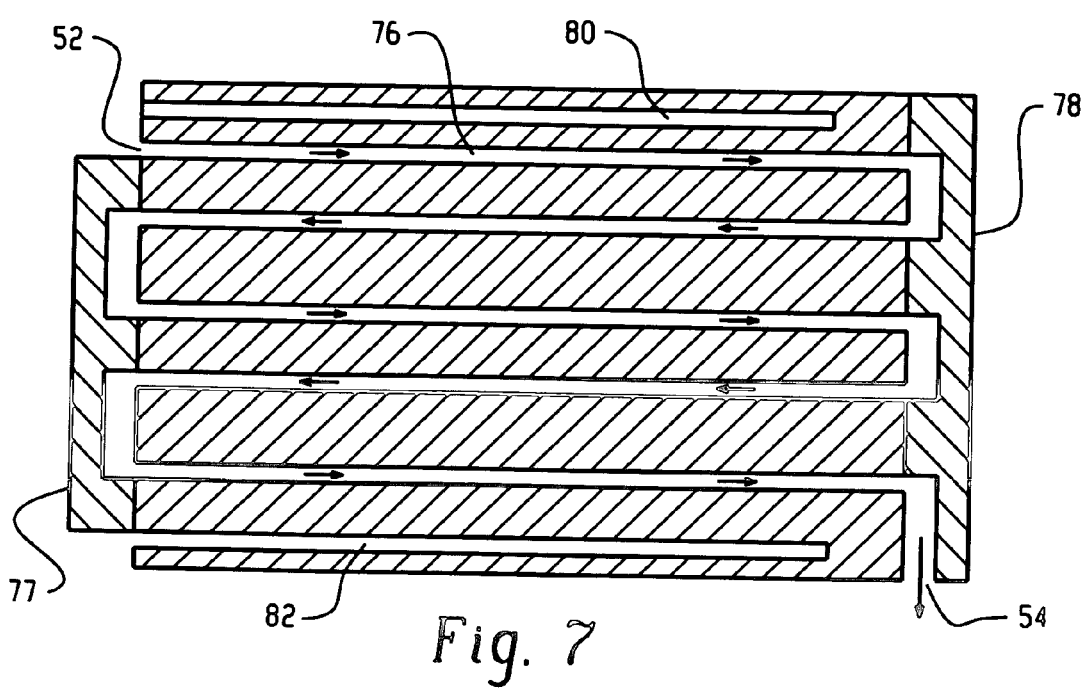
FIG. 7 is a side sectional view of a fifth vaporizer embodiment.

In an alternative embodiment, shown in FIG. 7, a bore 76 comprising one or more bore portions of uniform cross sectional area is provided, such that the entire bore or majority of the bore is of uniform cross sectional area. It is also contemplated that, for ease of manufacture, longitudinal bore portions may extend through the block, for example by drilling right through the block. The lateral portions are defined outside the block, by molded aluminum end pieces 77, 78, connecting tubing, or the like. The end pieces or connecting tubing are maintained at the temperature of the block and may be surrounded with a heating element, such as a heating tape with insulation, or the like.

With reference once more to FIGS. 2 and 3, block 50 is heated to a suitable temperature for vaporizing the liquid hydrogen peroxide. For example, heating elements 80, 82, 84, 86 are received in bores or passageways 88, preferably drilled longitudinally through the block adjacent the corners of the block. Suitable heating elements include electric resistance cartridge heaters. Such heaters are particularly appropriate for use as the heating element as they are commonly elongated and thin so that each heating element can be inserted into a heater bore and extend substantially from one end of the bore to the other. Alternatively, steam or another heated fluid is passed into heater bores to heat the block. The block is maintained by the heaters at a temperature below that at which significant dissociation of the hydrogen peroxide occurs.

Figure 8B:
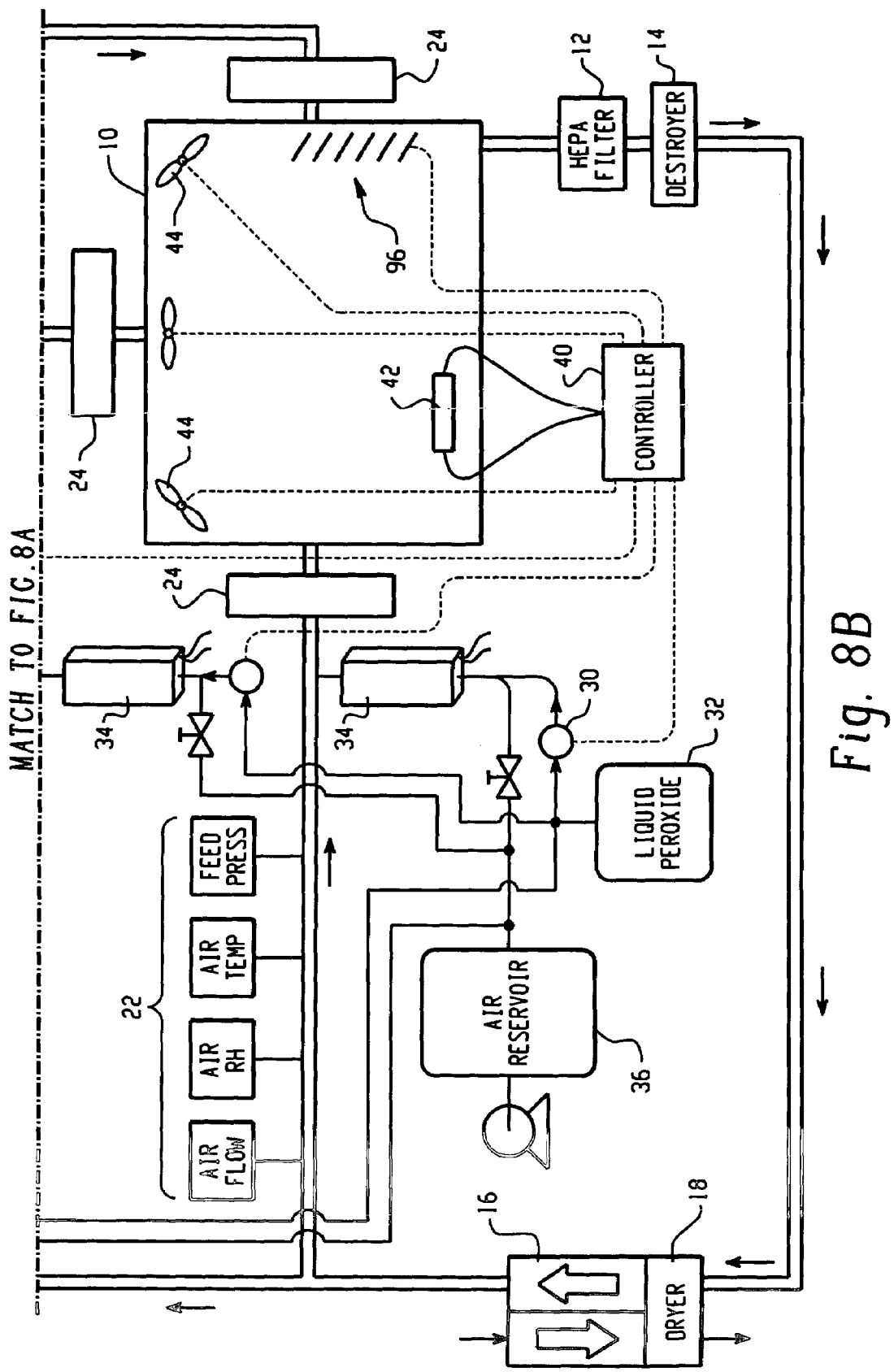
FIG. 8 is a diagrammatic illustration of an alternate system embodiment; and, FIG. 9 illustrates another alternate system embodiment.

The liquid hydrogen peroxide vaporizes as it contacts the wall of the bore and is progressively converted from a liquid, spray, or mist to a vapor. The increasing pressure which would normally result from this conversion is substantially eliminated by the increase in size of the bore and/or by an increase in flow velocity such that the flow through the bore is maintained. At the end of the series of passes through the block, the hydrogen peroxide is preferably entirely in vapor form at a temperature and pressure which maintain the vapor below the dew point, such that condensation of the vapor does not occur. The hydrogen peroxide vapor is then entrained in a flow of a carrier gas. Specifically, as shown in FIG. 8, the vapor travels along a line 90 to an injection port 92, or other suitable injection device, which injects the vapor into a carrier gas line 94 at a mixing zone. The injection port 92 is defined at the edge of the duct 94 with a minimal extension into the air flow to minimize air flow cooling of the injection port which could lead to condensation. The hydrogen peroxide vapor has sufficient velocity to be impelled substantially across the duct as the vapor is mixed into the flowing air. When multiple flash vaporizers are used, the injection ports may be located across from each other and offset from each other to create swirling turbulence, up/downstream from each other, or the like.

With continuing reference to FIG. 8, in another embodiment, air from blower 16 and dryer 18 is divided among a plurality of supply lines. Each line is equipped with a series of monitors 22, a flash vaporizer 34, and a HEPA filter 24 as described above. Each of the lines injects peroxide vapor into a different region of the room or building 10. Based on concentration readings sensed by the sensors 42, the controller 40 causes fans 44 or baffles 96 to channel more or less air flow through some of the returns relative to others. Corresponding adjustments are made to the rate of vapor generation and injection into each return.

In order to achieve a desired level of disinfection or sterilization, it is important for the hydrogen peroxide vapor to contact all potentially contaminated surfaces in the room. The surfaces may include the walls, floor, and ceiling of the room as well as various surfaces of shelving, equipment, stored materials, and the like inside of the room. Fans 44 are positioned to urge the hydrogen peroxide vapor entering the room to flow against all surfaces. Particular attention is paid to occluded and difficult to reach surfaces. Fans or baffles are preferably positioned to urge the peroxide vapor into corners, through narrow gaps, under shelves, around complex objects, into narrow fissures and crevices, and the like.

With reference again to FIG. 9, an open ended system is illustrated. A carrier gas is preferably air, although other gases which are unreactive towards hydrogen peroxide and the sterilized surfaces are also contemplated. A carrier gas generator 100 such as a pump or container of pressurized gas supplies the carrier gas to a duct 102. Microbe filters 104, such as HEPA filters, remove microbial and other particulate contaminants from the air. Preferably, a preheater 106 raises the temperature of the carrier gas. A dryer 108 preferably controls the humidity of the carrier gas. An adjustable baffle or gas flow regulator 110 controls the air flow rate to a peroxide absorption zone 112.

Liquid hydrogen peroxide (e.g., a water/hydrogen peroxide mixture) from a hydrogen peroxide supply 120 is pumped by a metering pump 122 to a mixing point 124 where it is mixed with filtered air from a blower 126 and a HEPA filter 128. The air and peroxide are injected into a flash vaporizer 34 as described above. The flash vaporizer injects hydrogen peroxide and water vapor through an injection port 130 into the absorption zone 112. Again, two or more vaporizers can be utilized to increase the rate of supply of peroxide gas to the absorption region.

Supply lines 140, 142 transport the mixture of carrier gas and vaporized hydrogen peroxide to a treatment site 144. To reduce the risk of condensation, the length of the supply lines 140, 142 is minimized. To reduce the risk of condensation further, insulation 146 and/or heaters 148 surround the supply lines 140, 142. Optionally, two or more supply lines connect each vaporizer to two or more regions of the enclosure 144. Optionally, the temperature of the carrier gas at the injection port may be increased to above the dew point of hydrogen peroxide.

A vent 150 permits controlled release of excess pressure in the enclosure. Optionally, a vacuum pump 152 evacuates the enclosure prior to hydrogen peroxide vapor introduction. Evacuation of the enclosure decreases the pressure and thus increases the diffusion rate of hydrogen peroxide therein. By reducing the pressure in the enclosure, one can minimize the need for baffles and/or fins at the point where the vaporized hydrogen peroxide is introduced into the enclosure. Alternatively, other types of pumps or blowers are used to help circulate and achieve a desired hydrogen peroxide concentration. Optionally, a catalyst 154 or the like breaks down any residual hydrogen peroxide in the vented gas. Optionally, a heater 156 raises the temperature of and within enclosure 144 prior to and during microbial decontamination. Raising the temperature in the enclosure or at least its surfaces also reduces the tendency for vapor to condense.

Sterilizable enclosures include microorganism-free work areas, freeze dryers, and pharmaceutical or food processing equipment. Whether high sterilization temperatures and/or evacuation of the enclosure during sterilization are feasible depends on the construction of the enclosure and the nature of its contents. For example, sterilizable work areas are, in some instances, constructed of non-rigid plastic materials which do not withstand high temperatures and large pressure gradients. Food processing equipment, in contrast, is often required to withstand high temperatures and pressures during processing operations and is more easily adapted to achieving more optimal sterilization conditions through evacuation and heating.

Figure 9:
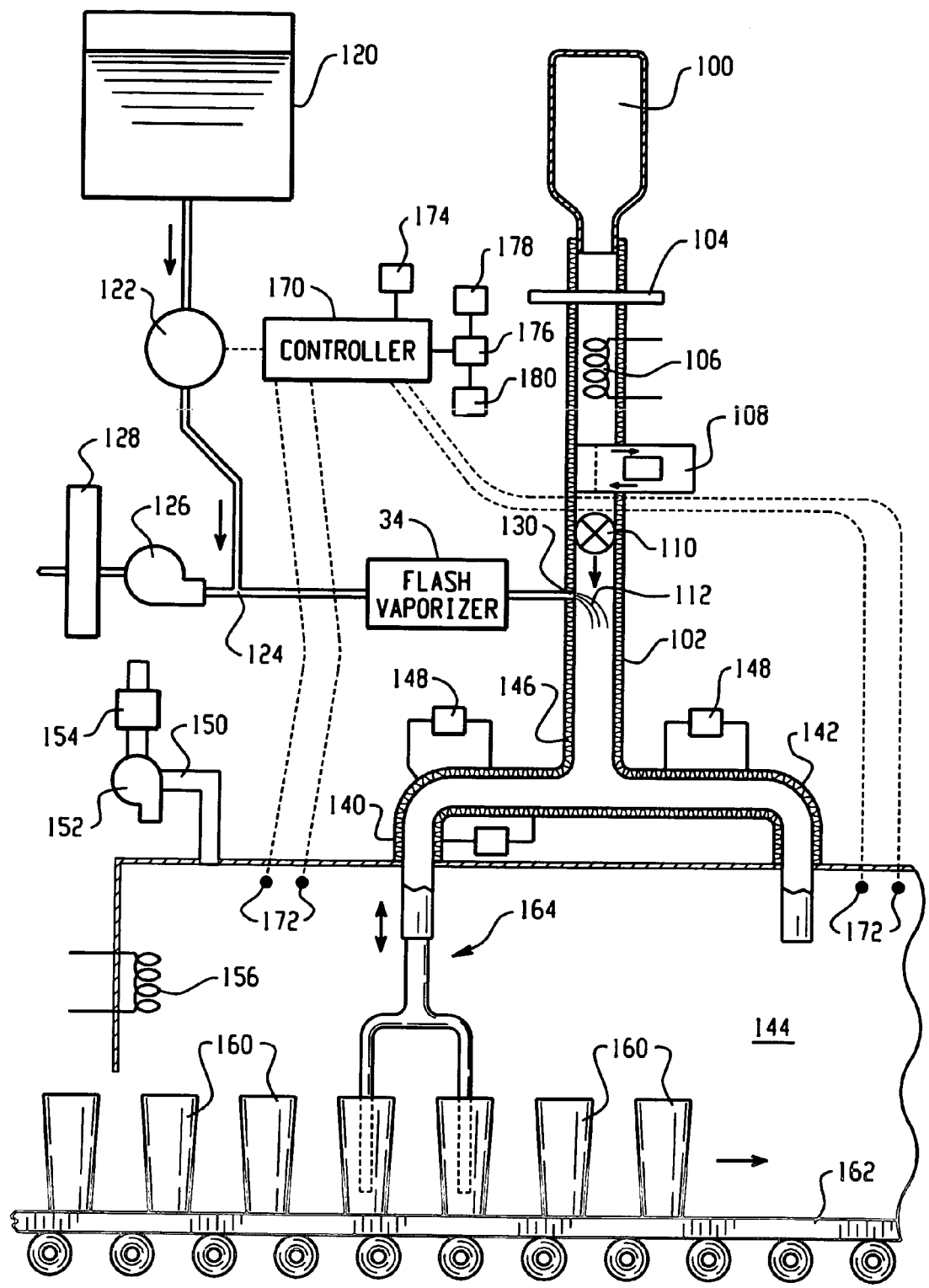

In FIG. 9, enclosure 144 is a portion of a packaging plant. Containers, such as bottles or cartons 160 are carried into the enclosure on a conveyor system 162. A reciprocating manifold 164 is connected with the each of the supply lines 140, 142 and sequentially raises and lowers a number of fill tubes or peroxide vapor injectors into the bottles or cartons as they pass or are indexed.

The hydrogen peroxide concentration in the solution is selected according to the desired vapor concentration. For example, the hydrogen peroxide concentration may be from 25–65% by weight aqueous hydrogen peroxide. In one embodiment, the hydrogen peroxide concentration is from about 30–35% by weight aqueous hydrogen peroxide. At this level, condensation of hydrogen peroxide is limited, while microbial decontamination is achieved in a short period of time.

In one embodiment, the hydrogen peroxide vapor is maintained at a concentration in the enclosure 144 until microbial decontamination is complete, and is continually replenished to maintain prescribed concentration levels. Optionally, the vacuum pump 152 draws out the hydrogen peroxide vapor from the enclosure following microbial decontamination. This reduces the time required for dissipation of the hydrogen peroxide, and returns the enclosure to useful activity more quickly. Alternatively or additionally, the enclosure is aerated, for example, by passing carrier gas alone through the enclosure, to remove any remaining hydrogen peroxide. In addition, a sensor may be employed to confirm that the enclosure has been aerated and that it may be returned to normal use.

Alternatively, once the hydrogen peroxide concentration of the enclosure has achieved a desired level, the vapor is held in the enclosure for a selected period of time sufficient to effect decontamination, without further additions of vapor to the enclosure or withdrawals of gas and/or vapor from the enclosure. For example, as shown in FIG. 1, valves 166, 168 in the vapor inlet and outlet lines leading to and from the enclosure are selectively closed once a selected vaporized hydrogen peroxide concentration is detected, and the hydrogen peroxide is held in the enclosure for a period of about one hour. For room-sized enclosures, in particular, it has been found that the hydrogen peroxide does not degrade or condense too rapidly in this time, such that microbial decontamination generally occurs throughout the holding period. The valves are then reopened and the remaining hydrogen peroxide is withdrawn. In a further embodiment, a series of two or more hold periods is used. In between each successive hold period, the hydrogen peroxide concentration is readjusted to the desired level.

In the illustrated embodiment, vaporizer 34 is preferably located in close proximity to the enclosure. Where more than one vaporizer is used, the rate of introduction of hydrogen peroxide by the individual vaporizers is adjustable so as to optimize hydrogen peroxide vapor distribution within the enclosure.

Differences in temperature and absorbency of materials within the enclosure, flow patterns in the enclosure, and enclosure shape are among the factors influencing the optimum rate of introduction. In the flow-through system of FIG. 9, the rate of throughput of containers or bottles through the enclosure also influences the optimum rate of peroxide introduction. Preferably, a control system 170 regulates the introduction of hydrogen peroxide to the flash vaporizer(s) 34 in accordance with detected conditions within the enclosure. A plurality of monitors 172 monitor conditions within the enclosure 144. The monitors include temperature sensors, humidity or vapor concentration sensors, air flow or turbulence sensors, pressure sensors, and the like. The control system includes a comparator 174 for comparing the monitored condition signals from the monitors with preselected ideal hydrogen peroxide vapor concentration and other conditions as indicated by reference signals. Preferably, the comparator determines a deviation of each monitored condition signal from the corresponding reference signal or a reference value. Preferably, a plurality of the conditions are sensed and multiple comparators are provided. A processor 176 addresses an algorithm implementing program or pre-programmed look up table 178 with each deviation signal (or combination of deviations of different conditions) to retrieve a corresponding adjustment for each flash vaporizer 34. Other circuits for converting larger deviations to larger adjustments and smaller deviations to smaller adjustments are also contemplated. Alternately, the error calculation can be made at very short intervals with constant magnitude increases or decreases when the monitored condition is below or above the reference points.

The adjustment values adjust the hydrogen peroxide metering pump 122 and the carrier gas regulator 110 to bring the monitored conditions to the reference values. For example, vapor injection rates are increased by vaporizers near regions with lower vapor concentration, higher temperatures, higher pressure, and the like. Vapor production rates are reduced in response to higher sensed vapor concentration, lower sensed temperatures, lower pressure, and the like. The processor, optionally, also controls the enclosure heater 156, circulation fans in the enclosure, the vacuum pump 152, or the like. Optionally, an operator input 180 enables the operator to adjust the reference signal in each region to cause higher or lower concentrations in selected regions.

Flash vaporizer 34 is capable of achieving a higher vapor output than conventional, drip-type vaporizers. For example, a heating block which supplies 1653 watts to the bores is able to vaporize 50 grams of hydrogen peroxide/minute (35% hydrogen peroxide, 65% water), since the heat of vaporization of the solution is 33.07 watt-min/gram. Obviously, as the heat supplied increases, correspondingly higher outputs can be achieved. Using one or more such vaporizers, a high speed bottling line (e.g., about 1000 bottles/min) can be decontaminated.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A vapor decontamination system for decontaminating a defined region, the system comprising:
   at least a first duct through which a first carrier gas flow passes to the defined region;
   an antimicrobial liquid source of a liquid which includes an antimicrobial compound;
   a compressed gas source of a compressed, second carrier gas different from the first carrier gas;
   a flash vaporizer which receives the liquid from the liquid source and the compressed second carrier gas from the compressed air source and creates a dispersion of the antimicrobial compound in the second carrier gas,
   an outlet of the flash vaporizer being connected to the duct for injecting the dispersion at a pressure higher than a pressure of the first carrier gas in the duct into the duct for absorption into the first carrier gas flow passing through the duct at a mixing zone downstream of the flash vaporizer.

2. The system as set forth in claim 1 wherein the antimicrobial compound includes hydrogen peroxide and the flash vaporizer includes:
   a metal block;
   at least one heater for heating and maintaining the metal block at or above a vaporization temperature of hydrogen peroxide and below a hydrogen peroxide disassociation temperature; and
   a passage extending through the block from an inlet to the outlet.

3. The system as set forth in claim 2 wherein the passage expands in cross section between the inlet and the outlet.

4. A vapor decontamination system for decontaminating a defined region, the system comprising:
   at least a first duct through which a first carrier gas flow passes to the defined region;
   a flash vaporizer for vaporizing a liquid which includes a hydrogen peroxide including antimicrobial compound into vapor, the flash vaporizer including:
   a metal block;
   at least one heater for heating and maintaining the metal block at or above a vaporization temperature of hydrogen peroxide and below a hydrogen peroxide disassociation temperature; and
   a passage that expands in cross section between the inlet and the outlet, extending through the block from an inlet to the outlet, the passage turning at least 180° between the inlet and the outlet;
   a second carrier gas flow connected with the flash vaporizer, an outlet of the flash vaporizer being connected to the duct for supplying a dispersion of the second carrier gas and vapor into the duct for absorption into the first carrier gas flow passing through the duct at a mixing zone downstream of the flash vaporizers; and,
   a means for introducing the liquid from a source to the flash vaporizer.

5. The system as set forth in claim 4 wherein the passage includes at least two turns of approximately 90° and a wall therebetween, such that the liquid in the passage strikes the wall, thereby increasing a vaporization rate of the liquid antimicrobial compound.

6. The system as set forth in claim 4 wherein the passage includes:
   a plurality of interconnected bores extending back and forth through the block between the inlet and the outlet.

7. The system as set forth in claim 1 further including:
   a heater and a dehumidifier connected with the duct upstream from the mixing zone.

8. The system as set forth in claim 6 further including:
   microbe trapping filters disposed adjacent the duct inlet and the duct outlet.

9. The system as set forth in claim 7 wherein the duct includes:
   an inlet upstream of the heater and the dehumidifier connected with the defined region such that the first carrier gas flow is circulated from the duct inlet, through the heater and dehumidifier, through the mixing zone, and through a duct outlet into the defined region.

10. The system as set forth in claim 6 wherein the antimicrobial compound includes hydrogen peroxide and further including:
a hydrogen peroxide destroyer for decomposing hydrogen peroxide vapor into water vapor and oxygen, the destroyer being disposed upstream from the dehumidifier.

11. A decontamination system for decontaminating a defined region, the system comprising:
at least a first duct through which a first carrier gas flow is passed from a first carrier gas source to the defined region;
a heated block that defines fluid passage for dispersing a liquid which includes an antimicrobial compound in a second carrier gas flow, the heated block fluid passage having an inlet and an outlet, the outlet of the block fluid passage being connected to the first duct for injecting a dispersion of the liquid in the second carrier gas into a turbulent mixing zone in the first duct at a higher pressure and a higher velocity than the first carrier gas flow to cause turbulent mixing and absorption of the dispersion into the first carrier gas flow; and
a source of the second carrier gas flow under pressure connected with the block inlet for creating a positive pressure differential from the heated block to the mixing zone, the second carrier gas source being different from the first carrier gas source.

12. The system as set in claim 11 further including:
a microbe trapping filter between the duct and the defined region.

13. The system as set forth in claim 1 further including:
at least one additional flash vaporizer and means for injecting an additional quantity of the dispersion into the duct.

14. The system as set forth in claim 1 further including:
at least a second flash vaporizer which forms a dispersion of the antimicrobial liquid and the second carrier gas and a second connecting duct connecting the second flash vaporizer to the second duct at a second mixing zone.

15. The system as set forth in claim 1 further including:
a first plurality of monitors connected with the duct upstream of the mixing zone;
a second plurality of monitors disposed in the defined region; and
a controller connected to the monitors for controlling the means for introducing liquid in accordance with monitored conditions in the duct and in the defined region.

16. The system as set forth in claim 11 further including:
fans disposed in the defined region for circulating vapor into partially occluded subregions.

17. The system as set forth in claim 11 wherein the means for introducing the liquid further including a metering pump which meters the liquid into the passage of the block.

18. A method of decontaminating a defined region, the method comprising:
pumping a first carrier gas stream through a duct to the defined region;
in a passage different from the duct, converting a liquid into an antimicrobial dispersion in a second carrier gas stream; and
injecting the formed antimicrobial dispersion into the first carrier gas stream at a lower flow rate and a higher velocity than the first carrier gas stream at a mixing zone defined in the duct upstream of the defined region to entrain the antimicrobial dispersion in the carrier gas.

19. The method as set forth in claim 18 wherein the first carrier gas stream flows through the duct is at a rate of at least 20 cubic meters per minute and the defined region is an enclosure of at least 10,000 cubic meters.

20. The method as set forth in claim 18 wherein the antimicrobial dispersion includes vapor phase hydrogen peroxide and further including:
heating a block which has an internal passage to a temperature sufficient to vaporize the hydrogen peroxide but which temperature is lower than a temperature which disassociates hydrogen peroxide;
passing hydrogen peroxide into the passage through the block to vaporize the hydrogen peroxide;
passing the hydrogen peroxide vapor from the passage into the mixing zone; and
mixing the hydrogen peroxide vapor into the carrier gas flow.

21. A method of decontaminating a defined region, the method comprising:
circulating a first carrier gas through a duct to the defined region;
in a passage different from the duct, converting a liquid into an antimicrobial dispersion which includes hydrogen peroxide in a second carrier gas from a different source than the first carrier gas;
blowing the hydrogen peroxide dispersion through the passage to create a positive pressure differential between the passage and the duct; and
injecting the antimicrobial dispersion from the passage into a mixing zone defined in the duct upstream of the defined region to entrain the antimicrobial dispersion in the first carrier gas.

22. The method as set forth in claim 20 further including heating and drying the carrier gas in the duct upstream of the mixing zone.

23. The method as set forth in claim 21 further including:
pulling carrier gas with antimicrobial dispersion from the enclosed area through a microbe-trapping filter; and
drying and heating the carrier gas and passing the dried, heated carrier gas to the duct upstream of the mixing zone.

24. The method as set forth in claim 23 further including anti-microbially filtering carrier gas between the duct and the defined region.

25. The method as set forth in claim 18 wherein the defined region is a large room and the duct includes existing HVAC duct work.

26. The method as set forth in claim 25 further including:
supplying carrier gas through a plurality of ducts into the room; and
injecting hydrogen peroxide dispersion into the carrier gas in each of the ducts.

27. The method as set forth in claim 18 further including:
directing antimicrobial dispersion in the defined region against at least one surface to be decontaminated.

28. The method as set forth in claim 18 further including:
monitoring concentration of the antimicrobial compound in the dispersion in the room and carrier gas conditions in the duct upstream of the mixing zone, and controlling a rate at which the antimicrobial dispersion is supplied to the duct in accordance therewith.

29. The method as set forth in claim 18 further including:
monitoring a concentration of the antimicrobial compound in the dispersion in the defined region until the concentration reaches a preselected level; and
holding the dispersion in the defined region without further addition of antimicrobial dispersion for a period of time.

30. The method as set forth in claim 18 further including:
heating a block above a vaporization temperature of a peroxy compound; and
metering the peroxy compound in liquid form into an internal bore in the block to vaporize the peroxy compound.

31. The method as set forth in claim 18 further including:
entraining a liquid peroxy compound into a controlled air flow in the passage.

32. The method as set forth in claim 31 wherein the passage turns and further including:
propelling peroxy compound droplets into heated passage surfaces at turns in the passage.

33. A method of decontaminating an enclosure comprising:
compressing a second carrier gas into a reservoir;
providing a first carrier gas stream and a stream of the second carrier gas from the reservoir, the second carrier gas stream having a lower flow rate than the first carrier gas stream;
introducing the second stream to a passage, the passage having at least one bend;
introducing a flow of an aqueous solution of a peroxy compound into the passage upstream of the bend, the peroxy compound mixing with the second stream, walls of the passage being heated to vaporize the aqueous solution forming a dispersion of the aqueous solution in the second carrier gas; and
injecting the dispersion into the first carrier gas stream with a sufficiently high velocity to cause turbulent mixing of the dispersion into the first carrier gas stream in a mixing zone and transporting the mixed dispersion and first carrier gas stream to the enclosure.

* * * * *